United States Patent [19]
Roemmele et al.

[11] Patent Number: 6,147,220
[45] Date of Patent: Nov. 14, 2000

[54] PROCESS TO 5-METHYLENEOXAZOLINES

[75] Inventors: Renee Caroline Roemmele, Maple Glen; Heather Lynnette Rayle, North Wales, both of Pa.

[73] Assignee: Rohm and Haas Company, Philadelphia, Pa.

[21] Appl. No.: 09/079,639

[22] Filed: May 15, 1998

Related U.S. Application Data

[60] Provisional application No. 60/047,343, May 21, 1997.

[51] Int. Cl.$^7$ ...................... C07D 263/08; C07D 413/02
[52] U.S. Cl. .................... 548/239; 548/235; 548/237; 548/238; 546/271.4; 544/182; 544/216; 544/238; 544/335; 544/336
[58] Field of Search ..................... 548/235, 237, 548/238, 239; 546/271.4; 544/182, 216, 238, 335, 336

[56] References Cited

U.S. PATENT DOCUMENTS 5,936,096  8/1999  Rayle et al. ........................ 548/239

FOREIGN PATENT DOCUMENTS

WO 95/19351  7/1995  WIPO .

OTHER PUBLICATIONS

Transformations of the Herbicide N–(1,1–dimethylpropynyl)–3,5–dichlorobenzamide in Soil, Roy Y. Yih, et al., *Weed Science*, vol. 18, Issue 5 (Sep.), 1970, pp. 604–607.

Identification of Metabolites of N–(1,1–dimethylpropynyl)–3,5–dichlorobenzamide in Soil and Alfalfa, Roy Y. Yih, et al., *J. Arg. Food Chem.*, vol. 19, No. 2, 1971, pp. 314–319.

*Primary Examiner*—Richard L. Raymond
*Assistant Examiner*—Brenda Coleman
*Attorney, Agent, or Firm*—Clark R. Carpenter

[57] ABSTRACT

This invention provides a process for the preparation of a 5-methylene-1,3-oxazoline from an alkyl ketone by reacting the alkyl ketone with an acetylating agent and an acid catalyst in an appropriate solvent and at an appropriate temperature. The resulting 5-methylene-1,3-oxazoline can be chlorinated and subsequently hydrolyzed to form an α-chloroketone which is useful as a fungicide.

21 Claims, No Drawings

PROCESS TO 5-METHYLENEOXAZOLINES

This application claims the benefit of U.S. Provisional Application No. 60/047,343, Filed May 21, 1997.

This invention relates to a process for the preparation of 5-methyleneoxazolines from alkyl ketones. The 5-methyleneoxazolines are useful intermediates for the preparation of a-chloroketones which can be utilized as fungicides.

Currently there is no known method disclosed for the formation of 5-methyleneoxazolines by ring closure of alkyl ketones of the type described herein. Oxazolines of the type mentioned can be obtained from acid or base catalyzed ring closure of alkynyl amides. Previously disclosed routes to these desired 5-methyleneoxazoline from substituted alkynyl amides required the use of strong and, consequently, expensive bases such as sodium hydride or sodium amide. These bases require the use of scrupulously anhydrous conditions and are difficult to handle. Additionally, yields of the 5-methyleneoxazoline from the alkynyl amide are unacceptably low for economic viability. Other disclosed routes to the desired 5-methyleneoxazoline from substituted alkynyl amides involve treatment of the amide with silver ion in N,N-dimethylformamide. This type of procedure uses an expensive and environmentally toxic catalyst and a solvent that requires a difficult work-up and produces large volumes of organic laden aqueous waste. Moreover, the alkyl ketone is sometimes formed as a by-product in these ring closures of alkynyl amides if sufficient water is present. The alkyl ketone can even become the dominant product if enough water is present. A convenient method for closing the alkyl ketone to the useful 5-methyleneoxazoline is therefore desirable.

We have discovered a simple solution to these problems. An alkyl ketone is dissolved in a solvent and an acid catalyst is added along with an acetylating agent and the resulting mixture reacted at an appropriate temperature. While not wishing to be bound by theory, we believe that during the course of the reaction an intermediate enol acetate is formed which subsequently closes to the 5-methyleneoxazoline. This intermediate is transient and only postulated, but the reaction does not proceed without the acetylating agent being present.

WO95/19351 discloses the formation of 2-aryl-5-methyleneoxazoline derivatives by cyclization of an alkynyl amide in the presence of a base. Yih et al. in *Weed Science*, 18, 604–607 (1970) and in *J. Agr. Food Chem.*, 19, 314–317 (1971) disclose the formation of aryl-5-methyleneoxazolines from a substituted alkynyl amides using acid, base or silver ion in an aqueous alcohol solution. However, the formation of such 5-methyleneoxazolines by cyclization of an alkyl ketone is not disclosed, taught or suggested.

This invention provides a process for the preparation of 5-methylene-1,3-oxazolines from alkyl ketones by reacting the alkyl ketone with an acetylating agent and an acid catalyst in an appropriate solvent and at an appropriate temperature. If desired, an excess of acetylating agent may be used as the solvent.

Specifically, this invention provides a process for the preparation of a 2-substituted-4,4-disubstituted-5-methylene-1,3-oxazoline of formula (I) by cyclization of an alkyl ketone of formula (II) in the presence of an acetylating agent, an acid catalyst, an appropriate solvent or excess acetylating agent, and an appropriate reaction temperature

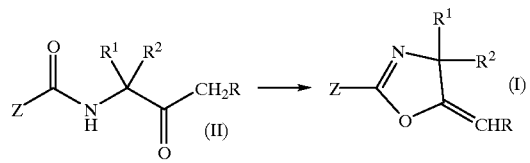

wherein

Z is alkyl or substituted alkyl, aryl or substituted aryl, heteroaryl or substituted heteroaryl or phenylene, R is a hydrogen atom or alkyl, and $R^1$ and $R^2$ are each independently an alkyl or substituted alkyl group, or $R^1$ and $R^2$ together with the carbon atom to which they are attached form a cyclic structure.

In this invention, alkyl means a $(C_1-C_8)$ straight or a $(C_3-C_8)$ branched chain alkyl group and includes, for example, methyl, ethyl, n-propyl, isopropyl, n-butyl, isobutyl, sec-butyl, tert-butyl, n-amyl, isoamyl, n-hexyl, isooctyl and the like. Substituted alkyl means an alkyl substituted with one or more substituents selected from the group consisting of alkoxy, halo, alkylthio and cyano.

Alkoxy means a $(C_1-C_4)$ straight or a $(C_3-C_4)$ branched chain alkyl group attached to an oxygen atom, for example, methoxy, ethoxy, isobutoxy and the like.

Alkylthio means a $(C_1-C_4)$ straight or a $(C_3-C_4)$ branched chain alkyl group attached to a sulfur atom, for example, methylthio, n-propylthio, sec-butylthio and the like.

Halo means bromo, chloro, fluoro and iodo.

Aryl means phenyl, naphthyl, or phenyl or naphthyl substituted with one to three substituents independently selected from the group consisting of halo, alkyl, alkynyl, alkoxy, nitro or cyano. Examples include, but are not limited to, phenyl, 2-naphthyl, 4-nitrophenyl, 4-chlorophenyl, 3,5-dimethylphenyl, 2,6difluorophenyl, 3,5-dichloro-4-methylphenyl, 3,5-dichlorophenyl, 3,5-difluorophenyl, 3,5-dibromophenyl, 3-chloro-4-ethyl-5-fluorophenyl, 3,5-dichloro-4-cyanophenyl, 3,5-dichloro-4-methoxyphenyl, 3,5-difluoro-4-propargylphenyl, 3,5-dibromo-4-methylphenyl and the like.

Alkynyl means a $(C_2-C_6)$alkynyl, for example, ethynyl, propargyl, 2-hexynyl and the like.

Heteroaryl means a 5-membered aromatic ring which may contain an oxygen atom, a sulfur atom, 1, 2 or 3 nitrogen atoms, an oxygen atom with 1 or 2 nitrogen atoms or a sulfur atom with 1 or 2 nitrogen atoms, or a 6-membered aromatic ring containing 1, 2 or 3 nitrogen atoms, or heteroaryl substituted with up to two substituents selected from halo, alkyl, haloalkyl or cyano. Examples include, but are not limited to 2-furyl, 2-thienyl, 4-chloro-2-thienyl, 2-oxazolyl, 2-imidazolyl, 1,2,4-triazol-1-yl, 2-imidazolyl, 2-pyrrolyl, 2-pyridyl, 3-pyridyl, 4-pyridyl, 4-pyridazinyl, 4-pyrimidinyl, 2-pyrazinyl, 1,3,5-triazin-2-yl, 4-chloro-3-pyridyl and the like.

Phenylene means 1,4-phenylene.

In a preferred form of this invention,

Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro and cyano, 2-naphthyl, 3-pyridyl and 1,4-phenylene, R is a hydrogen atom or a $(C_1-C_4)$alkyl, and $R^1$ and $R^2$ are each independently a $(C_1-C_4)$alkyl or $R^1$ and $R^2$ together with the carbon atom to which they are attached form a cyclopentyl or cyclohexyl ring.

In a more preferred form of this invention,

Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, 3-pyridyl or 1,4-phenylene, R is a hydrogen atom, methyl or ethyl, and $R^1$ and $R^2$ are each independently methyl or ethyl or $R^1$ and $R^2$ together with the carbon atom to which they are attached form a cyclohexyl ring.

In an even more preferred form of this invention,

Z is 4-chlorophenyl, 2,6-difluorophenyl, 3,5-dimethylphenyl, 3,5-dichloro-4-methylphenyl, 4-nitrophenyl, 1,4-phenylene, 2-naphthyl, 3-pyridyl or 3-heptyl, R is a hydrogen atom, and $R^1$ and $R^2$ are each independently methyl or ethyl.

The process of this invention is typically carried out by dissolving the alkyl ketone of formula (II) in the desired solvent followed by addition of the acetylating agent and the acid catalyst. The reaction is run at the chosen temperature until the reaction is complete based on gas chromatographic (GC) analysis. The reaction mixture is then partitioned between ethyl acetate and an aqueous base, typically saturated sodium bicarbonate, and the phases are separated. The aqueous phase is extracted once more, the organic phases are combined and are dried over a drying agent such as sodium sulfate. The drying agent is removed by filtration or centrifugation and the solvent is removed under reduced pressure to obtain the desired 5-methyleneoxazoline of formula (I).

The starting alkyl ketone of formula (II) can be prepared from an alkynyl amide by a procedure described in Yih et al., J.Agr. Food Chem., 19, 314–317 (1971). Preferred alkyl ketones of formula (II) are methyl ketones.

Solvents can be esters, for example ethyl acetate and butyl acetate, ethers, for example tert-butyl methyl ether, aliphatic hydrocarbons, for example heptane, chlorinated hydrocarbons, for example chloroform, aromatic hydrocarbons, for example toluene, or chlorinated aromatic compounds, for example monochlorobenzene. Preferred solvents are non-polar types such as aliphatic hydrocarbons, aromatic hydrocarbons and chlorinated aromatic hydrocarbons.

Any suitable acetylating agent can be used to form the postulated enol acetate intermediate. Preferred acetylating agents are acetic anhydride and isopropenyl acetate (1-propen-2-yl acetate). A more preferred acetylating agent is isopropenyl acetate. An excess of the acetylating agent may be employed in place of a solvent. When a solvent is employed, the amount of acetylating agent used is from about 1.0 equivalent to about 15 equivalents per equivalent of the alkyl ketone of formula (II). A preferred amount of acetylating agent is from about 1.25 equivalents to about 10 equivalents per equivalent of alkyl ketone. A more preferred amount of acetylating agent is from about 1.5 equivalents to about 5 equivalents per equivalent of alkyl ketone.

The acid catalyst used in the process can be a mineral acid, for example sulfuric acid, or an organic acid, for example methanesulfonic acid, ρ-toluenesulfonic acid, trichloroacetic acid and trifluoroacetic acid. Preferred acids are sulfuric acid, methanesulfonic acid and ρ-toluenesulfonic acid. The amount of acid catalyst used is from about 0.01 equivalent to about 1.5 equivalents per equivalent of alkyl ketone of formula (II). A preferred amount of acid catalyst is from about 0.02 equivalent to about 1.0 equivalent per equivalent of alkyl ketone. When sulfuric acid, methanesulfonic acid or ρ-toluenesulfonic acid is used, a more preferred amount of acid catalyst is about 0.05 equivalent per equivalent of alkyl ketone.

The reaction temperature is usually from about 20° C. to the reflux temperature of the solvent system employed. A preferred temperature is from about 25° C. to about 130° C. A more preferred temperature is from about 60° C. to about 120° C. An even more preferred temperature is from about 80° C. to about 100° C. when isopropenyl acetate is used as the acetylating agent. Pressure is not important, but the reaction is usually run at atmospheric pressure for convenience. The time of the reaction will depend upon the temperature employed, the substituent pattern of the starting alkyl ketone of formula (II), the solvent utilized, the nature of the acid catalyst, the type of acetylating agent, and the size and design of the reactor. However, the reaction is usually conveniently effected in a time of from about 30 minutes to about 5 days and more usually 3 days or less.

The following examples, tables and experimental procedures are provided for guidance to the practitioner and are not meant to limit the scope of the invention which is defined by the claims.

EXAMPLE 1

General Procedure Used for the Preparation of 5-Methylene-1,3-oxazolines from Alkyl Ketones To 1.0 g of starting alkyl ketone of formula (II) in 10 mL of solvent was added the acid catalyst and acetylating agent as shown in Table 1. The reaction was heated at the temperature indicated until complete by GC analysis. It was then partitioned between ethyl acetate and aqueous saturated sodium bicarbonate and the layers separated. The organic layer was washed with aqueous base (1×25 mL), then dried over sodium sulfate, filtered and the solvent removed under reduced pressure to obtain the 5-methyleneoxazoline of formula (I).

The physical properties of the 5-methyleneoxazolines made by this procedure are listed following Table 1.

TABLE 1

Preparation of 5-Methyleneoxazolines (I) from Alkyl Ketones (II)

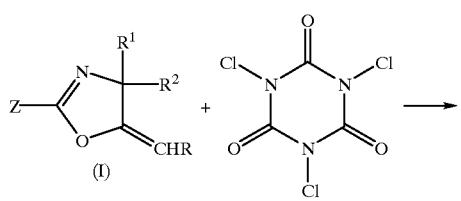

| Z | $R^1$ | $R^2$ | R | Solvent | Acetylating Agent (eq) [b.] | Catalyst (eq) [b.] | Time | Temp. | Weight Yield | Product Purity | SM [e.] |
|---|---|---|---|---|---|---|---|---|---|---|---|
| 3,5-Dichloro-4-methylphenyl | $CH_3$ | $C_2H_5$ | H | $CH_3CO_2C_4H_9$ | IPA [a.] (3) | $CH_3SO_3H$ (0.05) | 2 days | 100° C. | 89% [d.] | 100% | — |
| 3,5-Dichloro-4-methylphenyl | " | " | " | $CH_3CO_2C_4H_9$ | $(CH_3CO)_2O$ (3) | $CH_3SO_3H$ (0.05) | overnight | reflux | 100% [d.] | 80% | 20% |
| 3,5-Dichloro-4-methylphenyl | " | " | " | IPA [a.] | IPA | TsOH [c.] (0.05) | " | reflux | 100% [d.] | 100% | — |
| 3-heptyl | " | $CH_3$ | " | $(CH_3CO)_2O$ | $(CH_3CO)_2O$ | conc $H_2SO_4$ (0.05) | 1 hour | reflux | 97% [d.] | 88% | 9% |
| " | " | " | " | $CH_3CO_2C_2H_5$ | IPA (3) | $CH_3SO_3H$ (0.05) | overnight | reflux | 99% | 93% | — |
| " | " | " | " | $(CH_3)_3COCH_3$ | IPA (10) | conc $H_2SO_4$ (0.05) | " | reflux | 88% | 100% | — |
| " | " | " | " | $C_6H_5Cl$ | IPA (1.5) | $CH_3SO_3H$ (0.05) | " | 90° C. | 62% | 98% | — |
| " | " | " | " | $C_7H_{16}$ | IPA (2.0) | $CH_3SO_3H$ (0.05) | 5 hours | reflux | 97% | 96% | — |
| 4-nitrophenyl | " | " | " | $C_6H_5CH_3$ | IPA (3) | $CH_3SO_3H$ (0.05) | overnight | 90° C. | 90% | 98% | — |
| " | " | " | " | $CH_3CO_2C_2H_5$ | IPA (2) | $CH_3SO_3H$ (0.05) | " | reflux | 92% | 94% | — |
| " | " | " | " | $CHCl_3$ | IPA (2) | $F_3CCO_2H$ (0.5) | 2 days | reflux | 99% [d.] | 90% | 9% |
| " | " | " | " | $(CH_3)_3COCH_3$ | IPA (3) | $Cl_3CCO_2H$ (1) | 3 days | reflux | 100% [d.] | 54% | 46% |

[a.] IPA is isopropenyl acetate
[b.] Number in parentheses represents equivalents based upon ketone starting material
[c.] TsOH represents p-toluenesulfonic acid
[d.] Yield determined by gas chromatography
[e.] SM represents ketone starting material 2-(3,5-dichloro4-methylphenyl)-4-ethyl-4-methyl-5-methylene-1,3-oxazoline: bp (128° C., 1.0 mm); $^{13}C$ NMR (100 MHz, DMSO-$d_6$) δ165.1, 156.5, 137.6, 135.0, 126.5, 126.0, 83.9, 72.7, 34.0, 28.0, 17.4, 8.1.

2-(3-heptyl)-4,4-dimethyl-5-methylene-1,3-oxazoline: clear light brown liquid, $^1H$ NMR (400 MHz, CDCl$_3$) δ0.9 (t, 6H), 1.3 (m, 4H), 1.35 (s, 6H), 1.6 (m, 4H), 2.4 (m, 1H), 4.1 (d, 1H), 4.6 (d, 1H).

2-(4-nitrophenyl)-4,4-dimethyl-5-methylene-1,3-oxazoline: pale yellow solid mp=84.5–86° C., $^1H$ NMR (400 MHz, CDCl$_3$) 67 1.5 (s, 6H), 4.3 (d, 1H), 4.75 (d, 1H), 8.17 (d, 2H), 8.25 (d, 2H).

In a further aspect of this invention, the 5-methyleneoxazoline of formula (I) may be further reacted with a chlorinating agent, preferably trichloroisocyanuric acid (TCIA), to form a 5-(chloromethylene)oxazoline which is then hydrolyzed using an aqueous acid to produce an α-chloroketone. The resultant α-chloroketone is useful as a fungicide. Therefore, this invention further comprises the chlorination of a 5-methyleneoxazoline of formula (I) using TCIA as a chlorinating agent to produce a 5-(chloromethylene)oxazoline of formula (III)

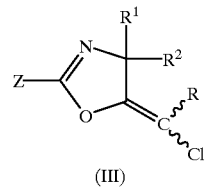

-continued

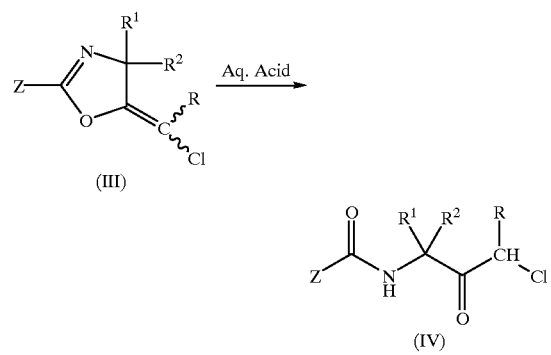

followed by the hydrolysis of the 5-(chloromethylene)oxazoline of formula (III) using an aqueous acid to produce an a-chloroketone of formula (IV)

wherein
  Z is alkyl or substituted alkyl, aryl or substituted aryl, heteroaryl or substituted heteroaryl or phenylene,
  R is a hydrogen atom or alkyl, and
  $R^1$ and $R^2$ are each independently an alkyl or substituted alkyl group, or $R^1$ and $R^2$ together with the carbon atom to which they are attached form a cyclic structure.

In this further aspect of the present invention, alkyl, substituted alkyl, alkoxy, alkylthio, aryl, alkynyl, heteroaryl and phenylene have the same meanings as stated previously.

In a preferred form of this further aspect of the present invention,

Z is ($C_1$–$C_8$)alkyl, phenyl or phenyl substituted with up to three substituents independently selected from the group consisting of halo, ($C_1$–$C_4$)alkyl, ($C_1$–$C_4$)alkoxy, ($C_2$–$C_6$)alkynyl, nitro and cyano, 2-naphthyl, 3-pyridyl and 1,4-phenylene, R is a hydrogen atom or a ($C_1$–$C_4$)alkyl, and $R^1$ and $R^2$ are each independently a ($C_1$–$C_4$)alkyl or $R^1$ and $R^2$ together with the carbon atom to which they are attached form a cyclopentyl or cyclohexyl ring.

In a more preferred form of this aspect of the present invention,

Z is 3-heptyl, phenyl, 4-halophenyl, 2,6-dihalophenyl, 4-($C_1$–$C_4$)alkylphenyl, 3,5-dihalophenyl, 3,5-di($C_1$–$C_4$)alkylphenyl, 4-($C_1$–$C_4$)alkyl-3,5-dihalophenyl, 4-cyano-3,5-dihalophenyl, 4-($C_1$–$C_4$)alkoxy-3,5-dihalophenyl, 4-nitrophenyl, 2-naphthyl, 3-pyridyl or 1,4-phenylene, R is a hydrogen atom, methyl or ethyl, and $R^1$ and $R^2$ are each independently methyl or ethyl or $R^1$ and $R^2$ together with the carbon atom to which they are attached form a cyclohexyl ring.

In an even more preferred form of this aspect of the present invention,

Z is 4-chlorophenyl, 2,6difluorophenyl, 3,5-dimethylphenyl, 3,5-dichloro-4methylphenyl, 4-nitrophenyl, 1,4-phenylene, 2-naphthyl, 3-pyridyl or 3-heptyl, R is a hydrogen atom, and $R^1$ and $R^2$ are each independently methyl or ethyl.

The chlorination step of the 5-methyleneoxazoline of formula (I) using TCIA may be performed at a temperature of from about –30° to about 100° C. A preferred chlorination temperature is from about 0° to 70° C. More preferred in order to obtain the best chlorination selectivity is a temperature of about 50° C. or lower. Even more preferred is a temperature from 0° to 30° C. The reaction is not pressure-dependent, but a pressure of 1 atmosphere is usually preferred for convenience. The stoichiometry of the reagents is extremely important. If less than 0.333 equivalent of TCIA per equivalent of 5-methyleneoxazoline is used, some of the 5-methyleneoxazoline starting material will remain unreacted. If greater than 0.333 equivalent is used, an overchlorinated intermediate is formed that leads to a dichloroketone after hydrolysis. The chlorination reaction time can vary from about 5 minutes to about 1 hour and is dependent on both the size and type of reactor equipment employed and the solvent used. The chlorination solvent is usually a polar solvent such as, but not limited to, an ether, an ester or a ketone, for example ethyl acetate, butyl acetate and methyl t-butyl ether. Preferred solvents are ethyl acetate or butyl acetate. Nonpolar solvents such as an aromatic hydrocarbon, for example toluene, or an aliphatic hydrocarbon, for example heptane and isooctane, may be also employed when admixed with a miscible polar type solvent or when heated to a temperature of about 40° C. After the chlorination reaction is carried out to the desired stage, the cyanuric acid by-product may be removed by filtration and/or by washing with a common base such as sodium carbonate, sodium hydroxide and the like. The resulting solution containing the 5-(chloromethylene)oxazoline is then subjected to the hydrolysis step.

In the hydrolysis step, a temperature of about 50° C. or higher is required. Preferably, the hydrolysis is performed from about 50° to 100° C. More preferably, the temperature employed is from about 50° to 80° C. Either an aqueous acid or a non-aqueous acid admixed with some water may be employed. A common acid such as, but not limited to, hydrochloric acid, sulfuric acid, trifluoroacetic acid, methanesulfonic acid or toluenesulfonic acid is convenient to use. Aqueous hydrochloric acid or sulfuric acid are preferred. An acidic ion-exchange resin may also be utilized. When hydrochloric acid or sulfuric acid are used, additional water is usually added to facilitate the hydrolysis. It is preferred that about 0.05 to 0.5 equivalent of an aqueous acid is used per equivalent of 5-chloromethyleneoxazoline. More preferred is the use of about 0.1 to 0.25 equivalent of aqueous hydrochloric acid per equivalent of 5-chloromethyleneoxazoline. The hydrolysis step usually takes from about 3 to about 24 hours, with the time depending on the nature of the Z group, the temperature and the size and nature of the equipment employed. The pressure used is not critical. However, 1 atmosphere is usually preferred for convenience.

In a typical representative reaction procedure for the chlorination and hydrolysis steps, the 5-methyleneoxazoline and solvent are combined and the resulting solution is chilled to 0–5° C. using an ice bath. The TCIA is added gradually, keeping the reaction temperature below 30° C. if possible. Once the TCIA has been added, the resulting slurry is warmed to room temperature and stirred until the reaction is complete based on (GC) analysis. The cyanuric acid by-product is removed by filtration and the solution is then washed with an appropriate base such as a sodium bicarbonate or sodium hydroxide solution to remove any remaining cyanuric acid. The solution containing the 5-(chloromethylene)oxazoline is returned to the flask and heated to 60° C. Concentrated hydrochloric acid and water are added and the solution is stirred until the hydrolysis is complete. The reaction mixture is cooled to room temperature and the desired α-chloroketone crystallizes on cooling. The solid obtained is filtered, washed and dried to give the product. A second crop is frequently obtained by concentration and cooling of the filtrate solution.

EXAMPLE 2

Representative Procedure Used for the Preparation of α-Chloroketones

Preparation of N-(1-chloro-3-methyl-2-oxobut-3-yl)-4-nitrobenzamide

A solution of 4,4-dimethyl-5-methylene-2-(4-nitrophenyl)oxazoline (10.0 g, 43.1 mmol) and ethyl acetate (35 mL) was cooled to 50° C. using an ice bath. Trichloroisocyanuric acid (3.33 g, 14.3 mmol) was added in several portions over 15 minutes in order to keep the reaction temperature below 40° C. When the addition was complete the reaction mixture was cooled to 20° C., and the ice bath was removed. The reaction was monitored by GC analysis for disappearance of the starting material. After 1.5 h, an additional 0.25 g (1.07 mmol) of the chlorinating agent was added in order to complete the chlorination. When the reaction was complete, the mixture was filtered. The filtrate was washed with ethyl acetate (15 mL). The filtrate was transferred to a round-bottom flask and heated to 60° C.; hydrochloric acid (0.85 g of a 37% solution) and water (2.8 mL) were added. The reaction mixture was stirred at 60° C. for 5 h, then cooled to room temperature. The resulting slurry was stored in a refrigerator overnight. The mixture was filtered, and the solids were rinsed with cold filtrate solution. The filtrate was concentrated to approximately half of its original volume by evaporation under reduced pressure. Hexane was gradually added until the solution clouded; the flask was chilled in a refrigerator at 8° C. overnight, then the slurry was filtered to obtain a second crop of crystals. Both crops were dried at 60° C. under vacuum, yielding N-(1-chloro-3-methyl-2-oxobut-3-yl)-4-nitrobenzamide (10.78 g, 88%) as a white solid, (mp 181–182° C.).

By following substantially the same procedure, the compounds shown in Table 2 were prepared from 5-methyleneoxazolines.

TABLE 2

Preparation of α-Chloroketones from a 5-Methyleneoxazoline and TCIA, Followed by Hydrolysis

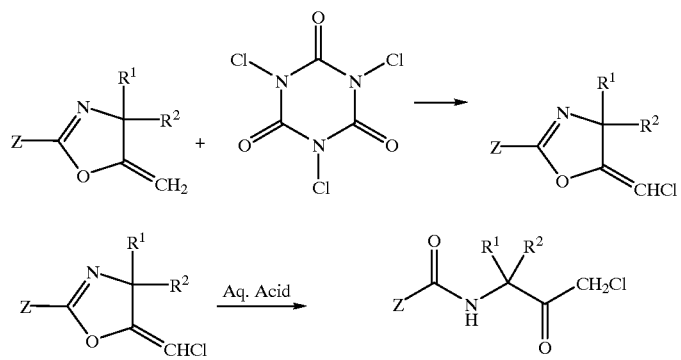

| Z | $R^1$ | $R^2$ | Product Yield (%) | mp (° C.) |
|---|---|---|---|---|
| 4-nitrophenyl | $CH_3$ | $CH_3$ | 88 | 181–182 |
| 4-chlorophenyl | $CH_2CH_3$ | $CH_3$ | 76 | 113–114 |
| 3,5-dimethylphenyl | $CH_3$ | $CH_3$ | 75 | 162–164 |
| 2,6-difluorophenyl | $CH_3$ | $CH_3$ | 75 | 191–192 |
| 2,6-difluorophenyl | —$(CH_2)_5$— | | 74 | 171–172 |
| 3,5-dicholoro-4-methylphenyl | $CH_2CH_3$ | $CH_3$ | 87 | 157–158 |
| phenyl | $CH_3$ | $CH_3$ | 74 | 154–155 |
| 3-heptyl | $CH_3$ | $CH_3$ | 58 | 58–60 |
| 2-naphthyl | $CH_3$ | $CH_3$ | 60 | 151–152 |
| 3-pyridyl | $CH_3$ | $CH_3$ | 85 | 128 (decomp.) |
| 1,4-phenylene | $CH_2CH_3$ | $CH_2CH_3$ | 60 | 193–196 |

It is to be understood that changes and variations in this invention may be made without departing from the spirit and scope of this invention as defined by the appended claims.

We claim:

1. A process for the preparation of a 2-substituted-4,4-disubstituted-5-methylene-1,3-oxazoline of formula (I) by cyclization of an alkyl ketone of formula (II) in the presence of an acetylating agent, an acid catalyst, an appropriate solvent or excess acetylating agent, and an appropriate reaction temperature

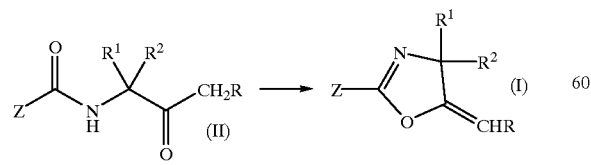

wherein

Z is alkyl or substituted alkyl, aryl or substituted aryl, heteroaryl or substituted heteroaryl, R is a hydrogen atom or alkyl, and $R^1$ and $R^2$ are each independently an alkyl or substituted alkyl group, or $R^1$ and $R^2$ together with the carbon atom to which they are attached form a cyclic structure.

2. The process of claim 1 wherein

Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro and cyano, 2-naphthyl, or 3-pyridyl, R is a hydrogen atom or a $(C_1-C_4)$alkyl, and $R^1$ and $R^2$ are each independently a $(C_1-C_4)$alkyl or $R^1$ and $R^2$ together with the carbon atom to which they are attached form a cyclopentyl or cyclohexyl ring.

3. The process of claim 2 wherein

Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C1-C4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, or 3-pyridyl, R is a hydrogen atom, methyl or ethyl, and $R_1$ and $R^2$ are each independently methyl or ethyl or $R^1$ and $R^2$ together with the carbon atom to which they are attached form a cyclohexyl ring.

4. The process of claim 3 wherein

Z is 4-chlorophenyl, 2,6-difluorophenyl, 3,5-dimethylphenyl, 3,5-dichloro-4-methylphenyl, 4-nitrophenyl, 2-naphthyl, 3-pyridyl or 3-heptyl, R is a hydrogen atom, and $R^1$ and $R^2$ are each independently methyl or ethyl.

5. The process of claim 1 wherein the solvent is an ester, an ether, an aliphatic hydrocarbon, a chlorinated hydrocarbon, an aromatic hydrocarbon or a chlorinated aromatic compound.

6. The process of claim 5 wherein the solvent is ethyl acetate, butyl acetate, tert-butyl methyl ether, heptane, chloroform, toluene, or monochlorobenzene.

7. The process of claim 1 wherein the acetylating agent is acetic anhydride or isopropenyl acetate.

8. The process of claim 1 wherein the acetylating agent is isopropenyl acetate.

9. The process of claim 7 wherein an excess of the acetylating agent is employed in place of a solvent.

10. The process of claim 1 using a solvent and from about 1.0 equivalent to about 15 equivalents of acetylating agent per equivalent of the alkyl ketone.

11. The process of claim 10 wherein the amount of acetylating agent is from about 1.25 equivalents to about 10 equivalents per equivalent of alkyl ketone.

12. The process of claim 1 wherein the acid catalyst is a mineral acid or an organic acid.

13. The process of claim 12 wherein the acid is sulfuric acid, or methanesulfonic acid, p-toluenesulfonic acid, trichloroacetic acid or trifluoroacetic acid.

14. The process of claim 13 wherein the acid is sulfuric acid, methanesulfonic acid or p-toluenesulfonic acid.

15. The process of claim 12 wherein the amount of acid catalyst used is from about 0.01 equivalent to about 1.5 equivalents per equivalent of alkyl ketone.

16. The process of claim 15 wherein the amount of acid catalyst is from about 0.02 equivalent to about 1.0 equivalent per equivalent of alkyl ketone.

17. The process of claim 14 wherein the amount of acid catalyst is about 0.05 equivalent per equivalent of alkyl ketone.

18. The process of claim 1 wherein the reaction temperature is from about 20° C. to the reflux temperature of the solvent system employed.

19. The process of claim 18 wherein the reaction temperature is from about 25° C. to about 130° C.

20. The process of claim 19 wherein the reaction temperature is from about 60° C. to about 120° C.

21. The process of claim 8 wherein the reaction temperature is from about 80° C. to about 100° C.

* * * * *